United States Patent [19]

Kemp

[11] Patent Number: 4,960,952
[45] Date of Patent: Oct. 2, 1990

[54] ALKOXYLATION PROCESS CATALYZED BY LANTHANUM SILICATES AND METASILICATES

[75] Inventor: Richard A. Kemp, Stafford, Tex.

[73] Assignee: Shell Oil Company, Houston, Tex.

[21] Appl. No.: 401,269

[22] Filed: Aug. 31, 1989

[51] Int. Cl.$^5$ ............................................. L07L 41/03
[52] U.S. Cl. ..................................... 568/618; 568/39;
  568/45; 568/608; 568/620; 568/622; 568/678;
  568/679; 560/263; 560/265; 560/200; 560/240;
  560/93; 560/209; 560/105; 560/112; 564/399;
  564/475; 564/505; 260/410.6; 530/217;
  530/232
[58] Field of Search ................... 568/39, 45, 608, 620,
  568/622, 678, 679; 560/93, 105, 112, 200, 240,
  263, 265; 564/399, 475, 505; 260/410.6;
  530/217, 232

[56] References Cited

U.S. PATENT DOCUMENTS

| | | | |
|---|---|---|---|
| 4,528,364 | 7/1985 | Prier | 528/370 |
| 4,658,065 | 4/1987 | Aoshima et al. | 564/487 |
| 4,665,236 | 5/1987 | Edwards | 568/618 |

FOREIGN PATENT DOCUMENTS 250168  12/1987  European Pat. Off. .

OTHER PUBLICATIONS

Y. Zhang, "Ring Opening Polymerization of Ethylene Oxide by the $Y(P_{204})_3$—$Al(i$—$Bu)_3$—$H_2O$ Catalyst", Inorganica Chemica Acta, 155 (1989), 263-265.

*Primary Examiner*—Howard T. Mars
*Attorney, Agent, or Firm*—Pamela J. McCollough

[57] ABSTRACT

Alkylene oxide adducts of organic compounds having active hydrogen atoms are prepared by a process which comprises contacting and reacting an alkylene oxide reactant comprising one or more vicinal alkylene oxides with an active hydrogen containing reactant comprising one or more compounds having active hydrogen atoms in the presence of a catalytically effective amount of one or more lanthanum compounds comprising silicate, metasilicate and mixtures thereof. The product alkoxylates are known to be useful, for instance, as nonionic surfactants, wetting and emulsifying agents, solvents, and chemical intermediates.

30 Claims, No Drawings

ALKOXYLATION PROCESS CATALYZED BY LANTHANUM SILICATES AND METASILICATES

FIELD OF THE INVENTION

This invention relates to an alkoxylation process in which alkylene oxides are reacted with compounds having active hydrogen atoms in the presence of catalysts comprising one or more lanthanum silicates and/or metasilicates. In particularly preferred embodiments, the invention relates to processes for the preparation of alkoxylate products useful as nonionic surfactants.

BACKGROUND OF THE INVENTION

A large variety of products useful, for instance, as nonionic surfactants, wetting and emulsifying agents, solvents, and chemical intermediates, are prepared by the addition reaction (alkoxylation reaction) of alkylene oxides (epoxides) with organic compounds having one or more active hydrogen atoms. For example, particular mention may be made of the alkanol ethoxylates and alkyl-substituted phenol ethoxylates prepared by the reaction of ethylene oxide with aliphatic alcohols or substituted phenols of about 6 to 30 carbon atoms. Such ethoxylates, and to a lesser extent corresponding propoxylates and compounds containing mixed oxyethylene and oxypropylene groups, are widely employed as nonionic detergent components of commercial cleaning formulations for use in industry and in the home. As another example, the addition reaction of propylene oxide with polyols provides intermediates for the preparation of polyurethane products.

An illustration of the preparation of an alkanol ethoxylate (represented by formula III below) by addition of a number (n) of ethylene oxide molecules (formula II) to a single alkanol molecule (formula I) is presented by the equation

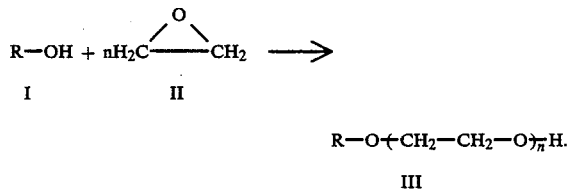

$$R-O(CH_2-CH_2-O)_{\overline{n}}H.$$

III

The addition of alkylene oxides to alcohols and other active hydrogen containing compounds is known to be desirably promoted by a catalyst which is in conventional practice either basic or acidic in character. Recognized in the art as suitable basic catalysts are the basic compounds of the alkali metals of Group I of the Periodic Table, e.g., sodium, potassium, rubidium, and cesium, and the basic salts of certain of the alkaline earth metals of Group II of the Periodic Table, e.g., calcium, strontium, barium and in some cases magnesium. Conventional acidic alkoxylation catalysts include, broadly, Lewis acid or Friedel-Crafts catalysts. Specific examples of these acid catalysts are the fluorides, chlorides, and bromides of boron, antimony, tungsten, iron, nickel, zinc, tin, aluminum, titanium and molybdenum. The use of complexes of such halides with, for example, alcohols, ethers, carboxylic acids, and amines has also been reported. Still other examples of known acidic alkoxylation catalysts are sulfuric and phosphoric acids; perchloric acid and the perchlorates of magnesium, calcium, manganese, nickel and zinc; certain metal oxalates, sulfates, phosphates, carboxylates and acetates, alkali metal fluoroborates., zinc titanate, and certain metal salts of benzene sulfonic acid.

Other art on the subject of alkoxylation includes U.S. Pat. No. 4,727,199, which describes a process for reacting a liquid or solid alkylene oxide with a liquid or gaseous active hydrogen compound in the presence of a catalytic amount of an anion-bound metal oxide heterogenous catalyst, wherein the anion is $SO_4$, $BF_4$, $CO_3$, $BO_3$, $PO_4$, $SeO_4$, $MoO_4$, $B_4O_7$ or $PF_6$ and the metal oxide is an oxide of zirconium, nickel, aluminum, tin, calcium, magnesium, iron, titanium, thorium, hafnium, or rubidium. Still other prior art describes the use of zeolitic materials as alkoxylation catalysts, while European patent application 0250168 and other art cited therein disclose lamellar clay catalysts.

Alkylene oxide addition reactions are known to produce a product mixture of various alkoxylate molecules having different numbers of alkylene oxide adducts (oxyalkylene adducts), e.g., having different values for the adduct number n in formula III above. The adduct number is a factor which in many respects controls the properties of the alkoxylate molecule, and efforts are made to tailor the average adduct number of a product and/or the distribution of adduct numbers within a product to the product's intended service. In certain preferred embodiments, the present invention provides a process characterized by enhanced selectivity for the preparation of alkoxylate mixtures in which a relatively large proportion of the alkoxylate molecules have a number (n) of alkylene oxide adducts that is within a relatively narrow range of values.

It is known in the art that alcohol alkoxylate products having a narrow range alkylene oxide adduct distribution are preferred for use in certain detergent formulations (Great Britain Pat. No. 1,462,134., Derwent Publications Research Disclosure number 194,010). Narrow-range alcohol alkoxylates are also known to be particularly valuable as chemical intermediates in the synthesis of certain carboxyalkylated alkyl polyethers (U.S. Pat. No. 4,098,818) and of certain alkyl ether sulfates (Great Britain Pat. No. 1,553,561). Conventional commercial alkoxylate preparation, which has in large part been limited to the use of basic catalysts, particularly the metals sodium and potassium and their oxides and hydroxides, yields only a relatively broad distribution range product. Conventional acid-catalyzed alkoxylation reactions have long been known to produce a more narrow range product than that obtained with the alkali metal catalysts. However, acid catalysts have substantial disadvantages in several other respects. For instance, the acids are often unstable with limited life and effectiveness as catalysts in the alkoxylation mixture. Both the acid catalysts themselves and their decomposition products catalyze side reactions producing relatively large amounts of polyalkylene glycols, and also react directly with the components of the alkoxylation mixture to yield undesirable, and often unacceptable, by-products such as organic derivatives of the acids.

Also of substantial importance in alkoxylation processes is the ability of the process to minimize the quantity of unreacted (or residual) active hydrogen reactant remaining in the final product. A high level of residual reactant either represents a loss of valuable reactant, or requires that further processing of the product be carried out to recover the reactant. Moreover, the presence of the unreacted material is often a disadvantage from the standpoint of product quality and environmental concerns. For instance, residual alkanol in a detergent alcohol ethoxylate product contributes to volatile organic emissions during spray drying of detergent formulations.

It has recently been reported in the art that, in addition to conventional acidic catalysts, a number of other substances have been found to function as catalysts or in co-catalyst combinations which are capable of producing relatively narrow distributions for the oxyalkylene adducts of higher alkanols and other active hydrogen containing compounds. For instance, it has recently been disclosed (U.S. Pat. Nos. 4,306,093 and and 4,239,917, and published European patent application Nos. 0026544, 0026546, 0026547) that certain compounds of barium, strontium, and calcium promote narrow-range alkoxylation products. U.S. Pat. Nos. 4,210,764 and 4,223,164 describe the use of cresylic acids to promote alkoxylation catalyzed by barium and strontium compounds. U.S. Pat. No. 4,302,613 discloses that a more peaked reaction product can be obtained by combining barium and strontium alkoxylation catalysts with co-catalysts such as calcium oxide, calcium carbide, calcium hydroxide, magnesium metal, magnesium hydroxide, zinc oxide and aluminum metal. U.S. Pat. No. 4,453,023 describes a process for preparing alkoxylates having a narrower molecular weight distribution which employs a catalyst comprising a barium compound and a promoter selected from the class consisting of superphosphoric acid, phosphoric acid, diphosphoric acid, triphosphoric acid, phosphorous acid, dihydrogen phosphate compounds, oxides of phosphorous, carbon dioxide, and oxalic acid. U.S. Pat. No. 4,453,022 describes a similar process wherein the catalyst comprises a calcium or strontium compound and a promoter selected from the class consisting of superphosphoric acid, phosphoric acid, diphosphoric acid, triphosphoric acid, phosphorous acid, dihydrogen phosphate compounds, oxides of phosphorus, sulfuric acid, bisulfate compounds, carbonic acid, bicarbonate compounds, carbon dioxide, oxalic acid and oxalic acid salts, sulfur trioxide, sulfur dioxide, and sulfurous acid. Published PCT application WO 85/00365 discloses other activated calcium containing alkoxylation catalysts capable of producing narrow range alkoxylation products. U.S. Pat. No. 4,375,564 reports that a narrow range product results from alkoxylation reactions catalyzed by a magnesium compound in combination with a compound of one of the elements aluminum, boron, zinc, titanium, silicon, molybdenum, vanadium, gallium, germanium, yttrium, zirconium, niobium, cadmium, indium, tin, antimony, tungsten, hafnium, tantalum, thallium, lead and bismuth. U.S. Pat. No. 4,483,941 discloses catalysts for alkoxylation reactions which comprise either $BF_3$ or $SiF_4$ in combination with an alkyl or alkoxide compound of aluminum, gallium, indium, thallium, titanium, zirconium, and hafnium. U.S. Pat. No. 4,456,697 describes an alkoxylation catalyst which comprises a mixture of HF and one or more metal alkoxides. Japanese patent specification 52051307 to Tokuyama Soda KK discloses the selective preparation of mono- rather than di- or tri-alkylene glycol esters from alkYlene oxide and alcohol using solid acid catalysts such as silica, alumina, titania, vanadium pentoxide, antimony pentoxide, titanyl sulfate, tungstic acid, phosphotungstic acid, and silver perchlorite.

Recently issued U.S. Pat. No. 4,721,816 claims a process for preparing narrow range distribution alkoxylates, wherein the catalyst is a combination of one or more sulfur-containing acids with one or more aluminum alcoholate or phenolate compounds. U.S. Pat. No. 4,721,817 claims a similar process wherein the combination contains one or more phosphorus-containing acids.

U.S. Pat. Nos. 4,665,236 and 4,689,435 describe a process for the alkoxylation of active hydrogen reactants using certain bimetallic oxo catalysts. With regard to the use in this invention of catalysts comprising one or more silicate salts of the element lanthanum, the catalysts described in U.S. Pat. No. 4,665,236 include compounds in which one of the metal species in the bimetallic molecule is lanthanum, and European application 0250168 discloses lamellar clay catalysts which have been ion exchanged with lanthanum and other rare earth elements.

SUMMARY OF THE INVENTION

It has now been found that lanthanum silicates and/or lanthanum metasilicates are effective catalysts for the addition reaction of alkylene oxides with organic compounds having active hydrogen atoms. It has further been found that, in certain preferred embodiments, an alkoxylation reaction catalyzed by a lanthanum silicate provides an alkoxylate product, particularly an alkanol ethoxylate product, of exceptionally narrow-range alkylene oxide adduct distribution.

The present invention is particularly directed to a process for the preparation of alkoxylates of active hydrogen containing organic compounds which comprises contacting an alkYlene oxide reactant comprising one or more vicinal alkylene oxides with an active hydrogen reactant comprising one or more organic compounds (e.g., alcohols, phenols, thiols, amines, polyols, carboxylic acids, etc.) having one or more active hydrogen atoms, in the presence of a catalytically effective amount of lanthanum in combination with one or more metal-free anions selected from the group consisting of silicate, metasilicate and mixtures thereof.

As used herein, the terms "silicate" and "metasilicate" refer to anions containing silica and oxygen and optionally, waters of hydration. It is understood that the silicates and metasilicates can have wide ranges of stoichiometries.

In general terms, the catalyst for the process of the invention comprises one or more of the silicate or metasilicate salts of the lanthanum. In particularly preferred embodiments, the catalyst additionally contains hydroxide and/or phosphate.

The lanthanum silicate and/or metasilicate salts are present in the alkoxylation mixture in catalytically effective amounts in either (or both) homogeneous or heterogeneous form(s), although heterogeneous catalysts have been found to be preferred in certain embodiments.

DESCRIPTION OF THE PREFERRED EMBODIMENTS

The present invention centers upon discoveries associated with the use in an alkoxylation process of a certain class of catalysts. Apart from the use of such catalysts, the process of the invention is, as a general rule, suitably conducted using such reactants and practicing under such processing procedures and reaction conditions as are well known to the art for alkoxylation reactions. Certain preferences may, however, be expressed for particular reactants, procedures and conditions.

Thus, for instance, the invention is preferably applied to processes utilizing an alkylene oxide (epoxide) reactant which comprises one or more vicinal alkylene oxides, particularly the lower alkylene oxides and more particularly those in the $C_2$ to $C_4$ range. In general, the alkylene oxides are represented by the formula

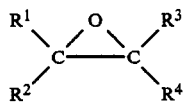

wherein each of the $R^1$, $R^2$, $R^3$ and $R^4$ moieties is individually selected from the group consisting of hydrogen and alkyl moieties. Reactants which comprise ethylene oxide, propylene oxide, or mixtures of ethylene oxide and propylene oxide are more preferred, particularly those which consist essentially of ethylene oxide and propylene oxide. Alkylene oxide reactants consisting essentially of ethylene oxide are considered most preferred from the standpoint of commercial opportunities for the practice of alkoxylation processes, and also from the standpoint of the preparation of products having narrow-range ethylene oxide adduct distributions.

Likewise, the active hydrogen reactants suitably utilized in the process of the invention include those known in the art for reaction with alkylene oxides and conversion to alkoxylate products. Suitable classes of active hydrogen reactants include (but are not necessarily limited to) alcohols, phenols, thiols (mercaptans), amines, polyols, carboxylic acids, and mixtures thereof. Preference generally exists for use of hydroxyl-containing reactants. More preferably, the active hydrogen containing reactant consists essentially of one or more active hydrogen containing compounds selected from the group consisting of alkanols, alkyl polyols and phenols (including alkyl-substituted phenols).

Among the suitable carboxylic acids, particular mention may be made of the mono- and dicarboxylic acids, both aliphatic (saturated and unsaturated) and aromatic. Specific examples include acetic acid, propionic acid, butyric acid, valeric acid, caproic acid, lauric acid, myristic acid, palmitic acid, steric acid, oleic acid, rosin acids, tall oil acids, terephthalic acid, benzoic acid, phenylacetic acid, toluic acid, acrylic acid, methacrylic acid, crotonic acid, maleic acid, and the like.

Among the suitable amines, particular mention may be made of primary, secondary and tertiary alkylamines and of alkylamines containing both amino and hydroxyl groups, e.g., N,N-di(n-butyl)-ethanolamine and tripropanolamine.

Among the suitable thiols, particular mention may be made of primary, secondary and tertiary alkane thiols having from 1 to about 30 carbon atoms, particularly those having from about 8 to 20 carbon atoms. Specific examples of suitable tertiary thiols are those having a highly branched carbon chain which are derived via hydrosulfurization of the products of the oligomerization of lower olefins, particularly the dimers, trimers, and tetramers and pentamers of propylene and the butylenes. Secondary thiols are exemplified by the lower alkane thiols, such as 2-propanethiol, 2-butanethiol, and 3-pentanethiols, as well as by the products of the hydrosulfurization of the substantially linear oligomers of ethylene as are produced by the Oxo process. Representative but not limiting examples of thiols derived from ethylene oligomers include the linear carbon chain products, such as 2-decanethiol, 3-decanethiol, 4-decanethiol, 5-decanethiol, 3-dodecanethiol, 5-dodecanethiol, 2-hexadecanethiol, 5-hexadecanethiol, and 8-octadencanethiol, and the branched carbon chain products, such as 2-methyl-4-tridecanethiol. Primary thiols are typically prepared from terminal olefins by hydrosulfurization under free-radical conditions and include, for example, 1-butanethiol, 1-hexanethiol, 1-dodecanethiol, 1-tetradecanethiol and 2-methyl-1-tridecanethiol.

Among the polyols, particular mention may be made of those having from 2 to about 6 hydroxyl groups. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like.

The alcohols (both mono- and poly-hydroxy) and the phenols (including alkyl-substituted phenols) are preferred classes of active hydrogen reactants for purposes of the invention. Among the phenols, particular mention may be made of phenol and of alkyl-substituted phenols wherein each alkyl substituent has from one to about 30 (preferably from one to about 20) carbon atoms, for example, p-methylphenol, p-ethylphenol, p-hexylphenol, nonylphenol, p-decylphenol, didecyl phenol and the like.

Acyclic aliphatic mono-hydric alcohols (alkanols) form a most preferred class of reactants, particularly the primary alkanols, although secondary and tertiary alkanols are also very suitably utilized in the process of the invention. Preference can also be expressed, for reason of both process performance and commercial value of the product, for alkanols having from one to about 30 carbon atoms, with $C_6$ to $C_{24}$ alkanols considered more preferred and $C_8$ to $C_{20}$ alkanols considered most preferred. As a general rule, the alkanols may be of branched or straight chain structure, although preference further exists for alkanol reactants in which greater than about 50 percent, more preferably greater than about 60 percent, and most preferably greater than about 70 percent of the molecules are of linear (straight-chain) carbon structure.

The general suitability of such alkanols as reactants in alkoxylation reactions is well recognized in the art. Commercially available mixtures of primary monohydric alkanols prepared via the oligomerization of ethylene and the hydroformylation or oxidation and hydrolysis of the resulting higher olefins are particularly preferred. Examples of commercially available alkanol mixtures include the NEODOL Alcohols, trademark of and sold by Shell Chemical Company, including mixtures of $C_9$, $C_{10}$ and $C_{11}$ alkanols (NEODOL 91 Alcohol), mixtures of $C_{12}$ and $C_{13}$ alkanols (NEODOL 23 Alcohol), mixtures of $C_{12}$, $C_{13}$, $C_{14}$, and $C_{15}$ alkanols (NEODOL 25 Alcohol), and mixtures of $C_{14}$ and $C_{15}$ alkanols (NEODOL 45 Alcohol); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418); and the TER- GITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Procter and Gamble Company and the TA alcohols of Ashland Oil Company.

Among the polyols, particular mention may be made of those having from 2 to about 6 hydroxyl groups and 2 or more, preferably 2 to 30 carbon atoms. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like. Higher oligomers and polymers of the polyols are also very suitable.

The active hydrogen containing reactant is also very suitably the alkoxylate product of a previous alkoxylation of an active hydrogen containing compound.

Further examples of both specific alkylene oxide reactants and specific active hydrogen containing reactants suitable for use in this invention are recited in the aforementioned U.S. Patents, the relevant disclosures of which are incorporated herein by this reference.

The alkylene oxide reactant and the active hydrogen reactant are necessarily contacted in the presence of compounds comprising lanthanum silicate, lanthanum metasilicate and mixtures thereof.

In addition to a catalytically effective amount of the lanthanum silicate and/or metasilicate, the catalyst for the process of the invention may also suitably contain other substances, including both those which may be introduced into the process as impurities in the silicate salt catalyst as well as those which may be added to promote or modify catalyst activity. The lanthanum silicate and/or lanthanum metasilicate may contain hydroxide and/or phosphate thus forming phosphate silicates, phosphate metasilicates, hydroxysilicates, hydroxymetasilicates, hydroxyphosphate silicates and hydroxyphosphate metasilicates.

The one or more of the silicate/metasilicate salts of lanthanum are present in the reaction mixture in a catalytically effective amount, i.e., an amount sufficient to promote the alkoxylation reaction or influence the alkylene oxide adduct distribution of the product. Although a specific quantity of catalyst is not critical to the invention, preference may be expressed for use of the catalyst in amount of at least about 0.01 percent by weight, while an amount between about 0.02 percent by weight and about 5.0 percent by weight is considered more preferred and an amount between about 0.1 percent by weight and about 2.0 percent by weight is considered most preferred for typical embodiments. These percentages are in terms of the weight of lanthanum ions in the process mixture relative to the weight of active hydrogen containing compounds in that mixture. Substantially greater quantities of catalyst, e.g., up to about 10 percent by weight or more, are also very suitable. As a rule, the higher the desired average alkylene oxide adduct number of the alkoxylate product and the higher the desired rate of reaction, the greater the required quantity of catalyst.

The silicate/metasilicate catalysts in the instant invention can suitably be prepared in any conventional manner such as, for example, by a metathesis reaction of a lanthanum salt such as lanthanum chloride and a silicate salt such as sodium silicate and/or a metasilicate salt such as sodium metasilicate. The catalysts are typically prepared by co-precipitation at a temperature of 25° C. In addition, hydroxide and/or phosphate can be added to the silicate and/or metasilicate. In a preferred embodiment, the catalyst is a silicate phosphate or a metasilicate phosphate.

In a particularly important embodiment, the invention is a process which comprises contacting and reacting an alkylene oxide reactant (particularly a reactant comprising ethylene oxide, propylene oxide, or a mixture of propylene oxide and ethylene oxide) with an active hydrogen containing reactant (particularly an alcohol, polyol, or other hydroxyl containing compound), in the presence of a catalyst which comprises one or more lanthanum compounds, at least one silicate or metasilicate anion and optionally, a phosphate and/or a hydroxide ion. In a most preferred embodiment, ethylene oxide is contacted with a $C_1$ to $C_{30}$ primary alkanol in the presence of a catalytically effective amount of such a compound.

In terms of processing procedures, the alkoxylation reaction in the invention may be conducted in a generally conventional manner. For example, the catalyst may initially be mixed with liquid active hydrogen reactant. The mixture of catalyst and liquid reactant is contacted, preferably under agitation, with alkylene oxide reactant, which is typically introduced in gaseous form, at least for the lower alkylene oxides. The order in which the reactants and catalyst are contacted has not been found to be critical to the invention.

While these procedures describe a batch mode of operation, the invention is equally applicable to a continuous process.

Overall, the two reactants are utilized in quantities which are predetermined to yield an alkoxylate product of the desired mean or average adduct number. The average adduct number of the product is not critical to this process. Such products commonly have an average adduct number in the range from less than one to about 30 or greater.

In general terms, suitable and preferred process temperatures and pressures for purposes of this invention are the same as in conventional alkoxylation reactions between the same reactants, employing conventional catalysts. A temperature of at least about 90° C., particularly at least about 120° C. and most particularly at least about 130° C., is typically preferred from the standpoint of the rate of reaction, while a temperature less than about 250° C., particularly less than about 210° C., and most particularly less than about 190° C., is typically desirable to minimize degradation of the product. As is known in the art, the process temperature can be optimized for given reactants, taking such factors into account.

Super-atmospheric pressures, e.g., pressures between about 10 and 150 psig, are preferred, with pressure being sufficient to maintain the active hydrogen reactant substantially in the liquid state.

When the active hydrogen reactant is a liquid and the alkylene oxide reactant is a vapor, alkoxylation is then suitably conducted by introducing alkylene oxide into a pressure reactor containing the liquid active hydrogen reactant and the catalyst. For considerations of process safety, the partial pressure of a lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between about 40 and 110 psig, with an alktlene oxide partial pressure between about 15 and 60 psig, is particularly preferred, while a total pressure of between about 50 and 90 psig, with an alkylene oxide partial pressure between about 20 and 50 psig, is considered more preferred.

The time required to complete a process according to the invention is dependent both upon the degree of alkoxylation that is desired (i.e., upon the average alkylene oxide adduct number of the product) as well as upon the rate of the alkoxylation reaction (which is, in turn dependent upon temperature, catalyst quantity and nature of the reactants). A typical reaction time for preferred embodiments is in the range from 1 to 24 hours.

After the ethoxylation reaction has been completed, the product is preferably cooled. If desired, catalyst can be removed from the final product, although catalyst removal is not necessary to the process of the invention. Catalyst residues may be removed, for example, by filtration, precipitation, extraction, or the like.

The following Examples are provided to further illustrate certain specific aspects of the invention but are not intended to limit its broader scope.

EXAMPLE 1

A lanthanum silicate catalyst was prepared by the following procedure. A first solution was prepared by dissolving 15.0 grams of lanthanum chloride ($LaCl_3 \cdot 7H_2O$: 40 mmoles) in 50 milliliters of deionized water. A second solution was prepared by dissolving 5.52 grams of sodium silicate ($Na_4SiO_4$: 30 mmoles) in 50 milliliters of water. The two solutions were then coprecipitated in a vessel containing 200 milliliters of water. A white precipitate formed immediately. The slurry was stirred for 30 minutes at room temperature and then filtered and washed with water. The solid formed was dried in a vacuum oven at 120° C. The material prepared was amorphous by x-ray diffraction.

An alkoxylation process in accordance with the invention was conducted under the following procedures. The alkylene oxide reactant for this process embodiment consisted of ethylene oxide and the active hydrogen containing reactant consisted of NEODOL 23 Alcohol (NEODOL is a trademark of Shell Chemical Company) characterized as a mixture of primary, 80% linear (20% branched), alkanols having twelve and thirteen carbon atoms (about 40% by mol $C_{12}$ and 60% by mol $C_{13}$).

Initially, 2.0 grams of the powder prepared as described above was added to 110 grams of NEODOL 23 Alcohol, and the mixture was heated in a 500 milliliter autoclave to 140° C. under nitrogen sparge to drive off water. A mixture of nitrogen and ethylene oxide was then introduced into the reactor to a total pressure of 75 psia (45 psia nitrogen and 30 psia ethylene oxide). Alkoxylation (ethoxylation) commenced immediately. Additional ethylene oxide was supplied on demand to maintain an essentially constant 75 psia pressure. Temperature was maintained at 140° C. A total of 90 grams of ethylene oxide was taken up over a period of 4.8 hours. The reactor was maintained for an additional 1 hour to consume unreacted ethylene oxide in the system.

The product was analyzed by GC-LC techniques and found to have a mean average adduct number of 3.2. The ethylene oxide adduct distribution of the product is presented in the following table. The only observed by-products were polyethylene glycols (PEG).

| ETHOXYLATE DISTRIBUTION | |
|---|---|
| Adduct Number | Concentration |
| 0 (Residual Alcohol) | 8.4% wt |
| 1 | 5.4 |
| 2 | 11.4 |
| 3 | 20.6 |
| 4 | 21.4 |
| 5 | 14.4 |
| 6 | 7.4 |
| 7 | 3.8 |
| 8 | 2.2 |
| 9 | 1.3 |
| 10 | 0.9 |
| 11 | 0.6 |
| 12 | 0.5 |
| 13 | 0.4 |
| 14 | 0.3 |
| 15 | 0.3 |

EXAMPLE 2

A lanthanum hydroxymetasilicate catalyst was prepared according to the following procedure. A first solution was prepared by dissolving 15.0 grams of lanthanum chloride ($LaCl_3 \cdot 7H_2O$: 40 mmoles) in 50 milliliters of deionized water. A second solution was prepared by dissolving 8.49 grams of sodium metasilicate ($Na_2SiO_3 \cdot 5H_2O$: 40 mmoles) in 50 milliliters of water. A third solution was prepared by dissolving 1.6 grams of sodium hydroxide (NaOH: 40 mmoles) in 50 milliliters of water. The three solutions were then simultaneously added to a vessel containing 200 milliliters of water. The white gelatinous precipitate formed was stirred at room temperature for 30 minutes. The slurry was filtered and the solids washed with 200 milliliters of deionized water. The solid formed was dried in a vacuum oven at 120° C.

Two grams of this powder was added to 110 grams of the NEODOL 23 Alcohol in a 500 milliliter autoclave, and the temperature of the mixture was ramped to 140° C. under nitrogen sparge to drive off water. The alcohol was ethoxylated at 140° C. and at a pressure of 75 psia (30 psia ethylene oxide and 45 psia nitrogen). A total of 188 grams of ethylene oxide was consumed over a period of 6 hours, yielding a product having a mean average adduct number of 6.7. The adduct distribution of this product is presented in the following table.

| ETHOXYLATE DISTRIBUTION | |
|---|---|
| Adduct Number | Concentration |
| 0 (Residual Alcohol) | 2.0% wt |
| 1 | 0.7 |
| 2 | 0.5 |
| 3 | 1.2 |
| 4 | 3.5 |
| 5 | 9.7 |
| 6 | 17.9 |
| 7 | 20.9 |
| 8 | 17.3 |
| 9 | 11.1 |
| 10 | 6.3 |
| 11 | 3.4 |
| 12 | 1.9 |

-continued

| ETHOXYLATE DISTRIBUTION | |
|---|---|
| Adduct Number | Concentration |
| 13 | 1.1 |
| 14 | 0.7 |
| 15 | 0.5 |

EXAMPLE 3

A lanthanum phosphate silicate catalyst was prepared under the following procedure. A first solution was prepared by dissolving 15.0 grams of lanthanum chloride ($LaCl_3 \cdot 7H_2O$: 40 mmoles) in 100 milliliters of deionized water. A second solution was prepared by dissolving 1.86 grams of sodium silicate ($Na_4SiO_4$: 10 mmoles) in 100 milliliters of water. A third solution was prepared by dissolving 10.2 grams sodium phosphate ($Na_3PO_4 \cdot 12H_2O$: 27 mmoles) in 100 milliliters of water. The three solutions were then simultaneously added during a 10 minute period to a vessel containing 200 milliliters of deionized water. The thick white gelatinous precipitate formed was stirred at room temperature for 30 minutes. The slurry was filtered and the solids washed with 600 milliliters of deionized water. The solid formed was dried in a vacuum oven at 120° C.

One gram of this powder was added to 110 grams of NEODOL 23 Alcohol. An ethoxylation reaction was then carried out according to the procedures described in Example 2. A total of 180 grams of ethylene oxide was consumed over a 4 hour period at a reaction temperature of 140° C. The product had a mean average adduct number of 6.6. The adduct distribution of this product is presented in the following table.

| ETHOXYLATE DISTRIBUTION | |
|---|---|
| Adduct Number | Concentration |
| 0 (Residual Alcohol) | 1.9% wt |
| 1 | 0.4 |
| 2 | 0.6 |
| 3 | 1.5 |
| 4 | 4.2 |
| 5 | 10.9 |
| 6 | 18.6 |
| 7 | 20.8 |
| 8 | 16.5 |
| 9 | 10.4 |
| 10 | 5.8 |
| 11 | 3.1 |
| 12 | 1.8 |
| 13 | 1.1 |
| 14 | 0.7 |
| 15 | 0.5 |

EXAMPLE 4

A mixed lanthanum phosphate metasilicate catalyst was prepared according to the following procedure. A first solution was prepared by dissolving 15 grams of lanthanum chloride ($LaCl_3 \cdot 7H_2O$: 40 mmoles) in 100 milliliters of deionized water. A second solution was prepared by dissolving 2.86 grams of sodium metasilicate ($Na_2SiO_3 \cdot 5H_2O$: 13.5 mmoles) in 100 milliliters of water. A third solution was prepared by dissolving 11.9 grams sodium phosphate ($Na_3PO_4 \cdot 12H_2O$: 31.4 mmoles) in 100 milliliters of water. The three solutions were then simultaneously added during a 10 minute period to a vessel containing 200 milliliters of water. The thick white gelatinous precipitate formed was stirred at room temperature for 30 minutes. The slurry was filtered and the solids washed with 600 milliliters of deionized water. The solid formed was dried in a vacuum oven at 120° C.

One gram of this powder was added to 110 grams of NEODOL 23 Alcohol. An ethoxylation reaction was then carried out according to the procedures described in Example 2. A total of 180 grams of ethylene oxide was consumed in 3 hours. The average adduct number of the product was 6.5 The adduct distribution of the product is presented in the following table.

| ETHOXYLATE DISTRIBUTION | |
|---|---|
| Adduct Number | Concentration |
| 0 (Residual Alcohol) | 1.9% wt |
| 1 | 0.5 |
| 2 | 0.9 |
| 3 | 1.5 |
| 4 | 4.7 |
| 5 | 12.6 |
| 6 | 20.5 |
| 7 | 20.7 |
| 8 | 14.8 |
| 9 | 8.5 |
| 10 | 4.7 |
| 11 | 2.7 |
| 12 | 1.7 |
| 13 | 1.1 |
| 14 | 0.8 |
| 15 | 0.7 |

What is claimed is:

1. A process for the preparation of alkylene oxide adducts of active hydrogen containing organic compounds, which comprises contacting and reacting an alkylene oxide reactant comprising one or more vicinal alkylene oxides with an active hydrogen containing reactant comprising one or more active hydrogen containing organic compounds, in the presence of a catalytically effective amount of one or more lanthanum compounds comprising lanthanum silicate, lanthanum metasilicate and mixtures thereof.

2. The process of claim 1 wherein the lanthanum compounds additionally comprise a compound selected from the group consisting of hydroxide, phosphate and mixtures thereof.

3. The process of claim 1 wherein said lanthanum compound comprises lanthanum silicate.

4. The process of claim 3 wherein said lanthanum silicate additionally comprises a compound selected from the group consisting of hydroxide, phosphate and mixtures thereof.

5. The process of claim 1 wherein said lanthanum compound is of lanthanum metasilicate.

6. The process of claim 5 wherein said lanthanum metasilicate additionally comprises a compound selected from the group consisting of hydroxide, phosphate and mixtures thereof.

7. The process of claim 1 wherein the alkylene oxide reactant consists essentially of one or more alkylene oxides selected from the group consisting of ethylene oxide and propylene oxide.

8. The process of claim 7 wherein the active hydrogen containing reactant consists essentially of one or more compounds selected from the group consisting of alkanols, phenols and polyols.

9. The process of claim 8 wherein the active hydrogen containing reactant consists essentially of one or more active hydrogen containing compounds selected from the group consisting of alkanols having from one to about 30 carbon atoms and alkyl-substituted phenols wherein each alkyl substituent has from one to about 30 carbon atoms.

10. The process of claim 9 wherein the active hydrogen containing reactant consists essentially of one or more $C_1$-$C_{30}$ primary mono-hydric alkanols.

11. The process of claim 10 wherein the active hydrogen containing reactant consists essentially of primary mono-hydric alkanols having carbon numbers in the range from 6 to 24, inclusive, and the alkylene oxide reactant consists essentially of ethylene oxide.

12. The process of claim 11 wherein the active hydrogen containing reactant consists essentially of primary mono-hydric alkanols having carbon numbers in the range from 8 to 20, inclusive.

13. The process of claim 12 wherein greater than about 50% of the molecules of the primary mono-hydric alkanols are of linear carbon structure.

14. The process of claim 13 wherein greater than about 70% of the molecules are of linear carbon structure.

15. A process for the preparation of alkylene oxide adducts of active hydrogen containing organic compounds, which comprises contacting and reacting an alkylene oxide selected from the group consisting of ethylene oxide and propylene oxide, with an active hydrogen containing reactant selected from the group consisting of alkanols, phenols and polyols, in the presence of a catalytically effective amount of lanthanum silicate.

16. The process of claim 15 wherein said lanthanum silicate additionally comprises a compound selected from the group consisting of hydroxide, phosphate and mixtures thereof.

17. The process of claim 15 wherein the active hydrogen containing reactant consists essentially of one or more active hydrogen containing compounds selected from the group consisting of alkanols having from one to about 30 carbon atoms and alkyl-substituted phenols wherein each alkyl substituent has from one to about 30 carbon atoms.

18. The process of claim 17 wherein the active hydrogen containing reactant consists essentially of one or more $C_1$-$C_{30}$ primary mono-hydric alkanols.

19. The process of claim 18 wherein the active hydrogen containing reactant consists essentially of primary mono-hydric alkanols having carbon numbers in the range from 6 to 24, inclusive, and the alkylene oxide reactant consists essentially of ethylene oxide.

20. The process of claim 19 wherein the active hydrogen containing reactant consists essentially of primary mono-hydric alkanols having carbon numbers in the range from 8 to 20, inclusive.

21. The process of claim 20 wherein greater than about 50% of the molecules of the primary mono-hydric alkanols are of linear carbon structure.

22. The process of claim 21 wherein greater than about 70% of the molecules are of linear carbon structure.

23. A process for the preparation of alkylene oxide adducts of active hydrogen containing organic compounds, which comprises contacting and reacting an alkylene oxide selected from the group consisting of ethylene oxide and propylene oxide, with an active hydrogen reactant selected from the group consisting of alkanols, phenols and polyols, in the presence of a catalytically effective amount of lanthanum metasilicate.

24. The process of claim 23 wherein said lanthanum metasilicate additionally comprises a compound selected from the group consisting of hydroxide, phosphate and mixtures thereof.

25. The process of claim 23 wherein the active hydrogen containing reactant consists essentially of one or more active hydrogen containing compounds selected from the group consisting of alkanols having from one to about 30 carbon atoms and alkyl-substituted phenols wherein each alkyl substituent has from one to about 30 carbon atoms.

26. The process of claim 25 wherein the active hydrogen containing reactant consists essentially of one or more $C_1$-$C_{30}$ primary mono-hydric alkanols.

27. The process of claim 26 wherein the active hydrogen containing reactant consists essentially of primary mono-hydric alkanols having carbon numbers in the range from 6 to 24, inclusive, and the alkylene oxide reactant consists essentially of ethylene oxide.

28. The process of claim 27 wherein the active hydrogen containing reactant consists essentially of primary mono-hydric alkanols having carbon numbers in the range from 8 to 20, inclusive.

29. The process of claim 28 wherein greater than about 50% of the molecules of the primary mono-hydric alkanols are of linear carbon structure.

30. The process of claim 29 wherein greater than about 70% of the molecules are of linear carbon structure.

* * * * *